United States Patent
Wang et al.

(10) Patent No.: US 11,517,690 B2
(45) Date of Patent: Dec. 6, 2022

(54) INFORMATION PROCESSING METHOD AND APPARATUS

(71) Applicant: BMC Medical Co., Ltd., Beijing (CN)

(72) Inventors: Yong Wang, Beijing (CN); Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 754 days.

(21) Appl. No.: 16/466,489

(22) PCT Filed: Oct. 30, 2017

(86) PCT No.: PCT/CN2017/108415
§ 371 (c)(1),
(2) Date: Jun. 4, 2019

(87) PCT Pub. No.: WO2018/103474
PCT Pub. Date: Jun. 14, 2018

(65) Prior Publication Data
US 2019/0314590 A1 Oct. 17, 2019

(30) Foreign Application Priority Data
Dec. 5, 2016 (CN) .......................... 201611105205.1

(51) Int. Cl.
*A62B 7/10* (2006.01)
*B01D 46/00* (2022.01)
(Continued)

(52) U.S. Cl.
CPC ........... *A61M 16/024* (2017.08); *G06F 40/12* (2020.01); *G06F 40/226* (2020.01); *H04W 4/80* (2018.02); *A61M 2205/60* (2013.01)

(58) Field of Classification Search
CPC ...... A61M 2230/205; A61M 2230/005; A61M 16/0051; A61M 16/024; A61M 2205/60;
(Continued)

(56) References Cited

U.S. PATENT DOCUMENTS

| | | | |
|---|---|---|---|
| 8,800,560 B2* | 8/2014 | Alfieri | A61M 16/0069 55/482 |
| 2005/0027568 A1* | 2/2005 | Dorris | G16H 40/20 705/3 |

(Continued)

FOREIGN PATENT DOCUMENTS

| CN | 103990212 A | 8/2014 |
|---|---|---|
| CN | 105022927 A | 11/2015 |

(Continued)

OTHER PUBLICATIONS

Battista et al., Preliminary evaluation of a wireless remote monitoring system for home mechanical ventilation, 6 pages (Year: 2016).*

(Continued)

*Primary Examiner* — Thuy Dao
(74) *Attorney, Agent, or Firm* — Nath, Goldberg & Meyer; Joshua B. Goldberg

(57) ABSTRACT

The embodiments of the present application provide an information processing method and apparatus, wherein the method is applied to a first client side, including: receiving therapy data from a therapy device, wherein the therapy data carries therapeutic effect data, a device identification corresponding to the therapy device, and a therapy parameter; sending the therapy data; and receiving parameter update information corresponding to the therapy data, wherein the parameter update information carries a latest therapy parameter acquired by updating the therapy parameter according to the therapeutic effect data, and the device identification corresponding to the therapy device. The embodiments of
(Continued)

```
┌─────────────────────────────────────────────────────────────────────┐  ─101
│ Receive therapy data from a therapy device, wherein the therapy     │
│ data carries therapeutic effect data, a device identification       │
│ corresponding to the therapy device, and a therapy parameter        │
└─────────────────────────────────────────────────────────────────────┘
                                  ↓
┌─────────────────────────────────────────────────────────────────────┐  ─102
│                       Send the therapy data                         │
└─────────────────────────────────────────────────────────────────────┘
                                  ↓
┌─────────────────────────────────────────────────────────────────────┐  ─103
│ Receive parameter update information corresponding to the therapy   │
│ data, wherein the parameter update information carries a latest     │
│ therapy parameter acquired by updating the therapy parameter        │
│ according to the therapeutic effect data, and the device            │
│ identification corresponding to the therapy device                  │
└─────────────────────────────────────────────────────────────────────┘
``` the present application can collect the therapy data of a user in time and conveniently, and improves the collecting efficiency of the therapy data.

10 Claims, 8 Drawing Sheets

(51) Int. Cl.
| | | |
|---|---|---|
| G06F 9/445 | (2018.01) | |
| G06F 9/455 | (2018.01) | |
| A61M 16/00 | (2006.01) | |
| H04W 4/80 | (2018.01) | |
| G06F 40/12 | (2020.01) | |
| G06F 40/226 | (2020.01) | |

(58) Field of Classification Search
CPC ..... A61N 1/3601; A61N 1/0556; H04W 4/80; G06F 40/12; G06F 40/226; A61B 17/12022; A61B 17/12172; A61B 17/12163; A61B 5/026; A61B 5/0809; A61B 5/4818; A61B 5/087; A61B 5/4848
See application file for complete search history.

(56) References Cited

U.S. PATENT DOCUMENTS

| | | | |
|---|---|---|---|
| 2010/0071696 A1* | 3/2010 | Jafari | A61B 5/087 |
| | | | 128/204.23 |
| 2010/0199102 A1 | 8/2010 | Knepper et al. | |
| 2014/0000609 A1* | 1/2014 | Steinhauer | G16H 20/17 |
| | | | 128/204.23 |
| 2018/0360314 A1* | 12/2018 | Wang | A61B 5/0024 |

FOREIGN PATENT DOCUMENTS

| | | |
|---|---|---|
| CN | 105031786 A | 11/2015 |
| CN | 105396208 A | 3/2016 |
| CN | 106534339 A | 3/2017 |
| CN | 106790437 A | 5/2017 |
| WO | 2015179915 A1 | 12/2015 |

OTHER PUBLICATIONS

European Office Action dated Oct. 22, 2019 for corresponding EP application 17878281.9.
First Office Action dated Jul. 3, 2019 Corresponding to Chinese Application No. 201611105205.1.
International Search Report; Application No. PCT/CN2017/108415; dated Jan. 31, 2018; English Translation Attached.

* cited by examiner

INFORMATION PROCESSING METHOD AND APPARATUS

This is a National Phase Application filed under 35 U.S.C. 371 as a national stage of PCT/CN2017/108415, filed Oct. 30, 2017, an application claiming the benefit of Chinese Application No. 201611105205.1, filed Dec. 5, 2016, the content of each of which is hereby incorporated by reference in its entirety.

TECHNICAL FIELD

The present application relates to the field of communication technologies, and more particularly, to an information processing method and apparatus.

BACKGROUND

A positive airway pressure ventilation therapy machine is used to treat sleep apnea syndrome and snoring, the working process of which mainly includes a therapy part and a support part. In the therapy part, a large amount of therapy data during the therapy process will be recorded. In the support part, therapy parameters will be adjusted and fed back to a patient's therapy device by collecting and analyzing the therapy data recorded in the therapy part.

At present, the therapy data is usually collected by such methods like wired transmission, removable storage medium, etc.

However, the wired transmission method either requires doctors or service personnel to carry a dedicated device to the patient for data collection, or requires the patient to carry the therapy device to a designated place for data collection, which wastes time, efforts and money. The transmission method of the removable storage medium is relatively cumbersome to operate, requiring the patient to download and store the therapy data in the removable storage medium, and then send the therapy data to the doctors or the service personnel by mail, etc. However, there is a time lag in the sending process, such that the therapy data of the patient cannot be acquired in time. Similarly, the patient is unable to acquire feedback information from the doctors on the therapy parameters of the patient.

SUMMARY

In view of the above problems, the embodiments of the present application are proposed so as to provide an information processing method and apparatus overcoming the above problems or at least partially solving the above problems, which can collect therapy data of users in time and conveniently, and improve the efficiency of collecting the therapy data.

The embodiments of the present application disclose an information processing method applied to a first client side, including:

receiving therapy data from a therapy device, wherein the therapy data carries therapeutic effect data, a device identification corresponding to the therapy device, and a therapy parameter;

sending the therapy data; and receiving parameter update information corresponding to the therapy data, wherein the parameter update information carries a latest therapy parameter acquired by updating the therapy parameter according to the therapeutic effect data, and the device identification corresponding to the therapy device.

According to another aspect, the embodiments of the present application disclose an information processing method applied to a second client side, including:

receiving therapy data from a first client side, wherein the therapy data carries therapeutic effect data generated by the therapy device, a device identification corresponding to the therapy device, and a therapy parameter; and sending parameter update information acquired for the therapy data to the first client side, wherein the parameter update information carries a latest therapy parameter acquired by updating the therapy parameter according to the therapy data, and the device identification corresponding to the therapy device.

According to still another aspect, the embodiments of the present application disclose an information processing apparatus applied to a first client side, including:

a first data receiving module configured to receive therapy data from a therapy device, wherein the therapy data carries therapeutic effect data, a device identification corresponding to the therapy device, and a therapy parameter;

a first data sending module configured to send the therapy data; and a first parameter receiving module configured to receive parameter update information corresponding to the therapy data, wherein the parameter update information carries a latest therapy parameter acquired by updating the therapy parameter according to the therapeutic effect data, and the device identification corresponding to the therapy device.

According to yet another aspect, the embodiments of the present application disclose an information processing apparatus applied to a second client side, including:

a second data receiving module configured to receive therapy data from a first client side, wherein the therapy data carries therapeutic effect data generated by the therapy device, a device identification corresponding to the therapy device, and a therapy parameter; and a second parameter sending module configured to send parameter update information acquired for the therapy data to the first client side, wherein the parameter update information carries a latest therapy parameter acquired by updating the therapy parameter according to the therapy data, and the device identification corresponding to the therapy device.

The embodiments of the present application include the following advantages.

According to the embodiments of the present application, the therapy data from the therapy device is received through the first client side, and the therapy data is sent, for example, to a device such as a server or the second client side or the like. Since the therapy data carries the therapeutic effect data, device identification corresponding to the therapy device and the therapy parameter, doctors can update the therapy parameter according to the therapeutic effect data to acquire the latest therapy parameter, such that the users can receive the latest therapy parameter corresponding to the therapy data through the first client side, so that the users can use the latest therapy parameter for therapy. The therapy data can be automatically collected through the embodiments of the present application, which does not requires the doctors or service personnel to carry dedicated devices to the users for data collection, or requires the users to carry therapy devices to a designated place for data collection, and can feed back the latest therapy parameter to the users in time. Therefore, the embodiments of the present application can collect the therapy data of the users in time and conveniently, improve the efficiency of collecting the therapy data, and acquire the parameter update information corresponding to the therapy data in time.

DETAILED DESCRIPTION

In order to understand the above objects, features and advantages of the present application more clearly, the present application will be described in further detail below with reference to the drawings and detailed description.

First Method Embodiment

Figure 1:
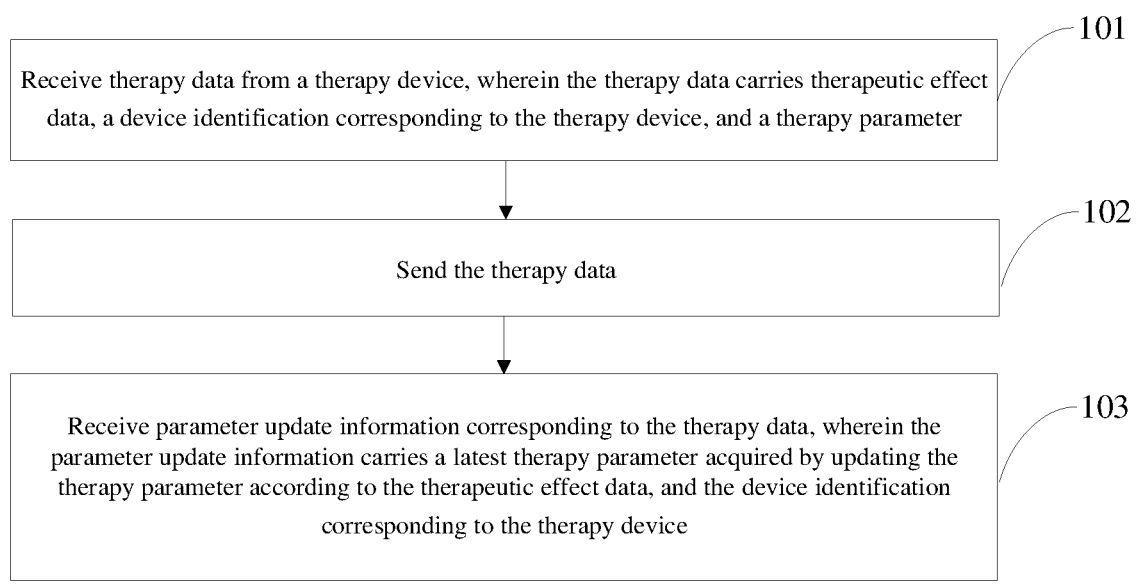
FIG. 1 is a flow chart of steps of an information processing method according to one embodiment of the present application.

FIG. 1 illustrates a flow chart of steps of an information processing method according to one embodiment of the present application. The method may be applied to a first client side, and may specifically include the following steps.

In step 101, therapy data from a therapy device is received, wherein the therapy data carries therapeutic effect data, a device identification corresponding to the therapy device, and a therapy parameter.

In the embodiment of the present application, the first/second client side may specifically be various types of smart terminals such as a smart phone, a tablet computer, and a notebook computer. The first client side is a smart terminal on a patient side, and the second client side is a smart terminal on a doctor side. It can be understood that the specific forms of the smart terminal are not limited in the embodiment of the present application. For convenience of description, the embodiments of the present application are all illustrated by taking smart phones as examples, and other application scenarios can be cross-referenced.

The therapy device may specifically be a device having a therapeutic function such as a positive airway pressure ventilation therapy machine (hereinafter referred to as the therapy machine) or a ventilator, which can be used to treat a patient and generate therapy data during the therapy process. Optionally, data may be transmitted between the first client side and the therapy device by short-range wireless communication. For example, the first client side may receive the therapy data from the therapy device through a wireless short wave such as Bluetooth or infrared. Of course, the data may further be transmitted between the first client side and the therapy device in a manner such as 3G ($3^{rd}$-Generation, $3^{rd}$ Generation Mobile Communication Technology), 4G (4th-Generation, $4^{th}$ Generation Mobile Communication Technology), WiFi (WIreless-Fidelity), etc. The embodiment of the application does not limit the data transmission mode between the first client side and the therapy device.

In step 102, the therapy data is sent.

In the embodiment of the present application, after the first client side receives the therapy data from the therapy device, the therapy data may be uploaded, so that a doctor can acquire the therapy data, and gives a further therapy schedule. Specifically, the first client side may send the therapy data to a server or the second client side. The server may be configured to manage the therapy data uploaded by a patient, and the therapy data carries the therapeutic effect data, the device identification corresponding to the therapy device and the therapy parameter. In this way, the doctor can log in the server to view the therapy data of the patient, analyze the therapeutic effect data therein to acquire an analysis result, and adjust the existing therapy schedule according to the analysis result, i.e., update the therapy parameter to acquire a latest therapy parameter. Of course, in order to enable the doctor to acquire the therapy data of the patient in time, the first client side can directly send the therapy data of the patient to the second client side on the doctor side. It can be understood that a specific device for the first client side to upload the therapy data is not limited in the embodiment of the present application.

In a specific application, the first client side and the server can communicate through an Ethernet network. The first client side and the second client side can communicate through any network such as 3G, 4G, WiFi, etc. Due to the wide application of network technologies and smart terminals, therapy data of users can be collected in time and conveniently by using data processing and data transmission capabilities of the smart terminals, and the therapy data can be transmitted through the network, without requiring the doctors or service personnel to carry dedicated devices to the users for data collection, or requires the users to carry therapy devices to a designated place for data collection, which brings great convenience for collecting the therapy data.

In step 103, parameter update information corresponding to the therapy data is received, wherein the parameter update information carries a latest therapy parameter acquired by updating the therapy parameter according to the therapeutic effect data, and the device identification corresponding to the therapy device.

Specifically, the first client side may receive the parameter update information corresponding to the therapy data returned by the doctor through the server or the second client side, so that the patient can acquire the feedback information given by the doctor for the therapy data in time and conveniently.

Further, in an optional embodiment of the present application, the method may further include the following steps.

The latest therapy parameter is sent to the therapy device corresponding to the device identification, and the therapy device is set according to the latest therapy parameter.

In actual application, after the doctor updates the therapy parameter to acquire the latest therapy parameter, the parameter update information may be returned to the first client side through the server or the second client side, and the first client side may send the latest therapy parameter to the corresponding therapy device, so that the parameter update information corresponding to the therapy data can be fed back to the therapy device of the user in time and become effective in the therapy device. Optionally, after the first client side receives the parameter update information corresponding to the therapy data, the first client side may send the latest therapy parameter to a therapy machine corresponding to the device when the device is connected next time, and automatically amend original parameters in the therapy machine, and set the therapy machine according to the latest therapy parameter without needing the patient to amend the parameters manually, which simplifies the operation of the users and brings convenience to the users. Of course, in practical application, the first client side may also send the latest therapy parameter to the corresponding therapy machine, and the user operates the therapy machine to make the latest therapy parameter become effective.

Optionally, the first client side may further receive an analysis result sent by the doctor through the server or the second client side for the user to view. Further, when receiving the parameter update information, the first client side may also prompt the user to promptly view the analysis result and the latest therapy parameter.

In an optional embodiment of the present application, in order to simplify the operation of the doctor, the first client side according to the embodiment of the present application may further analyze the therapy data, and the method may further include the following steps.

In step S11, the therapy data is analyzed to acquire an analysis result.

In step S12, the analysis result is sent, wherein the analysis result carries the device identification corresponding to the therapy device, and the therapy parameter.

In step S13, parameter update information corresponding to the analysis result is received, wherein the parameter update information carries a latest therapy parameter acquired by updating the therapy parameter according to the analysis result, and the device identification corresponding to the therapy device.

After the first client side receives the therapy data from the therapy device, the therapy data may be analyzed to acquire an analysis result, and the analysis result may be displayed by the first client side, and uploaded to the server or the second client side, so that the doctor can acquire the therapy data and the corresponding analysis result of the patient, so that the therapy parameter can be updated directly according to the analysis result, without requiring the doctor to manually analyze the therapy data, thus improving the working efficiency of the doctor.

In conclusion, according to the embodiments of the present application, the therapy data from the therapy device is received through the first client side, and the therapy data is sent, for example, to a device such as a server or the second client side or the like. Since the therapy data carries the therapeutic effect data, device identification corresponding to the therapy device and the therapy parameter, doctors can update the therapy parameter according to the therapeutic effect data to acquire the latest therapy parameter, such that the users can receive the latest therapy parameter corresponding to the therapy data through the first client side, so that the users can use the latest therapy parameter for therapy. The therapy data can be automatically collected through the embodiments of the present application, which does not requires the doctors or service personnel to carry a dedicated device to the users for data collection, or requires the users to carry a therapy device to a designated place for data collection, and can feed back the latest therapy parameter to the users in time. Therefore, the embodiments of the present application can collect the therapy data of the users in time and conveniently, improve the efficiency of collecting the therapy data, and acquire the parameter update information corresponding to the therapy data in time.

In addition, the first client side may be a smart terminal. Due to the wide application of the smart terminal, the smart terminal can be used for data collection and transmission without adding an additional wireless transmission module to the therapy device, thereby saving hardware costs.

First Application Example

Figure 2:
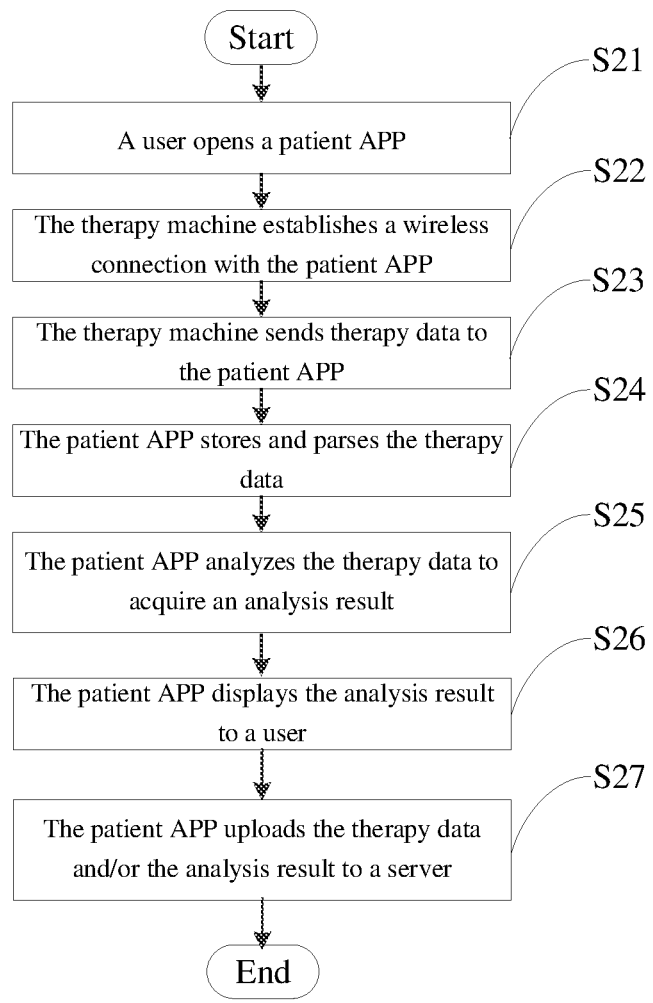
FIG. 2 is a schematic flow chart of uploading therapy data of a positive airway pressure ventilation therapy machine to a service platform according to the present application.

A process of uploading the therapy data of the therapy machine through the smart terminal in the present application will be described below with reference to a specific example. In this example, uploading the therapy data to the server by the first client side is taken as an example for description. FIG. 2 illustrates a schematic flow chart of uploading therapy data of a positive airway pressure ventilation therapy machine to a service platform according to the present application, which may specifically include the following steps.

In step S21, a user opens a patient APP.

In specific application, the patient APP (Application) can be installed in a first client side, and the patient APP can communicate with the therapy machine through a wireless short wave to transmit the data safely and rapidly. The patient APP can also analyze therapy data to acquire an analysis result, display the analysis result to a user, and upload the therapy data and the analysis result to a server. In practical application, the patient APP can analyze, display, and upload all data generated during the therapy process to the server, such as blood oxygen, pulse rate, pressure, air leak, snoring events, hypopnea events, apnea events, etc.

In step S22, the therapy machine establishes a wireless connection with the patient APP, such as a Bluetooth connection.

In step S23, the therapy machine sends the therapy data to the patient APP through the wireless connection.

In step S24, the patient APP stores and parses the received therapy data.

In specific application, the therapy data may include compliance data in addition to the therapeutic effect data, and the compliance data feeds back an implementation effect of the patient on a therapy schedule given by the doctor, such as: days to use the therapy machine in a month, hours to use the therapy machine in every day, what time to use the therapy machine, and whether to use the therapy machine intermittently during the therapy, so that the patient APP can comprehensively analyze the therapy data and the compliance data to acquire a more accurate analysis result.

In step S25, the patient APP analyzes the received therapy data to acquire an analysis result.

For example, the patient APP can give the following analysis result: a percentage of effective therapy days is 60%, which needs to be improved; an average daily use time is 4.4 hours, an effective AHI (average apnea hypopnea index) relative to the therapy time is 6, and a therapeutic effect is good (1-5 health), or the like.

In specific application, due to different sizes and types of the therapy data, different analysis methods can be used, for example, there are both data (frequency, duration, etc.) and waveforms after parsing the snoring data; but there are only waveforms after parsing pressure data. Specific forms for analyzing the therapy data are not limited in the embodiment of the present application.

In step S26, the patient APP displays the analysis result to the user.

In step S27, the patient APP uploads the therapy data and/or the analysis result to the server through 3G, 4G, or WiFi.

Second Method Embodiment

Figure 3:
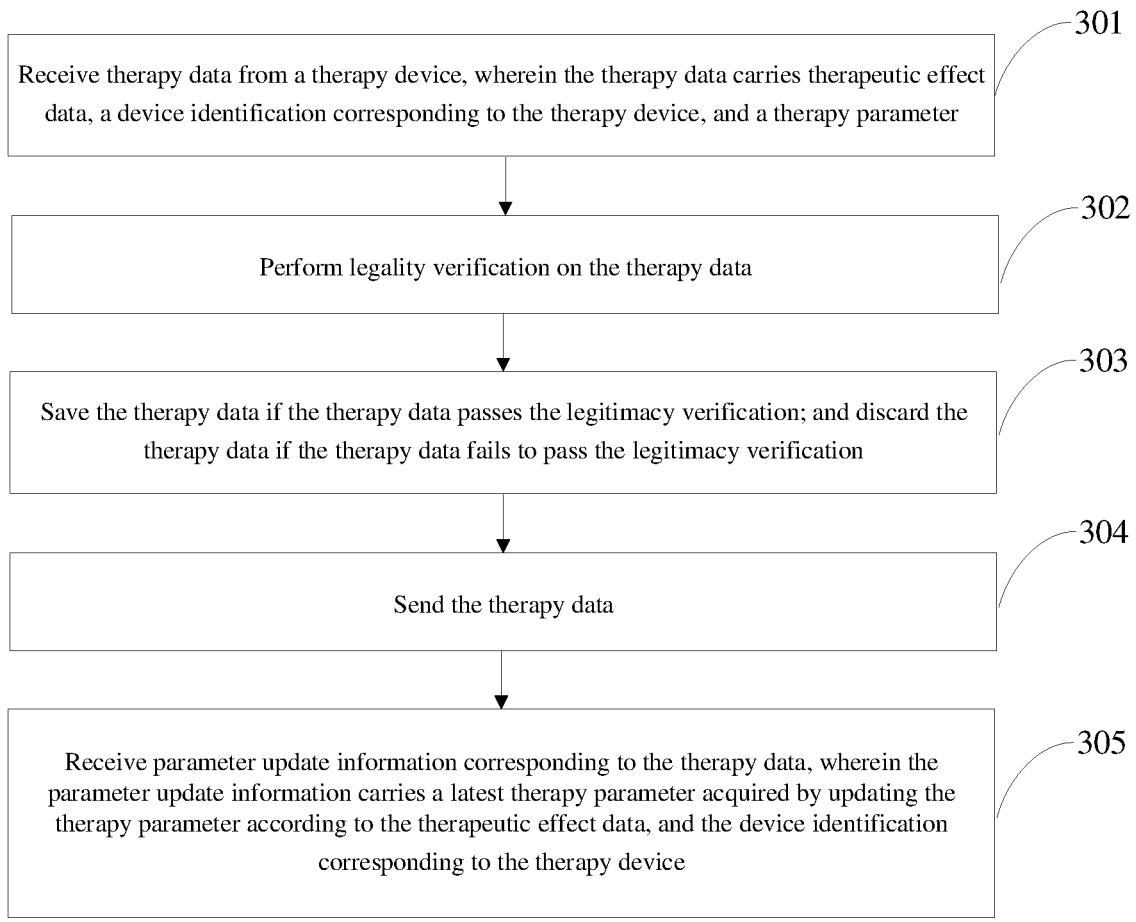
FIG. 3 is a flow chart of steps of an information processing method according to another embodiment of the present application.

In an optional embodiment of the present application, in order to improve the security of therapy data transmission, after a smart terminal receives the therapy data, legality verification may be further performed on the therapy data. FIG. 3 illustrates a flow chart of steps of an information processing method according to another embodiment of the present application. The method may be applied to a first client side, and may specifically include the following steps.

In step 301, therapy data from a therapy device is received, wherein the therapy data carries therapeutic effect data, a device identification corresponding to the therapy device, and a therapy parameter.

In step 302, legality verification is performed on the therapy data.

In the embodiment of the present application, the therapy data may be encapsulated according to a customized data format. Optionally, the therapy data may specifically be configured in that a plaintext string is formed for a digital content in the therapeutic effect data by a preset format, an original check code is generated by a preset algorithm according to the plaintext string and a device identification of the therapy device, such as a CRC16 (Cyclic Redundancy Check), and then the original check code is combined with the plaintext string to acquire iCode (Information Coding).

The information coding iCode refers to a process of giving a code to an information element while transforming original information symbols according to a certain mathematical rule, so as to facilitate the storage, retrieval and use of the information. It can be understood that the above process of acquiring the information coding is only used as an application example of the present application. In specific application, a specific manner of the information coding is not limited in the present application.

In specific application, the therapy data transmitted between the therapy device and the smart terminal can be verified according to a customized data format and a conventional algorithm to prevent the data content from being maliciously falsified. In addition, the patient APP can also support a background operation mode to ensure data integrity, and store the data in a specific file to ensure the confidentiality of the data and prevent the data from being destroyed by other applications.

The plaintext string may specifically include at least one of a statistical period, a percentage of effective therapy days, an average daily use time, an average therapy pressure, an average apnea hypopnea index, a percentage of high air leak time, and a time of continuously using the therapy device in the statistical period being greater than a given maximum number of days.

In an application example of the present application, it is assumed that a machine number of a therapy machine used by the user is 1209D105, and therapy data generated by the therapy machine includes: a statistical period is 90 days, a percentage of effective therapy days is 60%, an average daily use time is 4.4 hours, a P95 (Average Therapy Pressure) is 10.5 hPa, an AHI (Average Apnea Hypopnea Index) is 6, a percentage of high air leak time is 22%, and a Best 30 (a time of continuously using the therapy device in the statistical period being greater than a given maximum number of days) is 21.

The therapy machine generates a 13-bit plaintext string (4604421062221) according to the digital content in the above-mentioned therapy data, and then generates a 3-bit check code (243) by a preset algorithm according to the plaintext string and the machine number, and finally obtains complete iCode information coding (4604421062221243). Table 1 shows a specific illustration of iCode information coding according to an application example of the present application.

TABLE 1

| Item | Number of bits | Description |
| --- | --- | --- |
| iCode type | 1 | Indicating a statistical period of iCode data, wherein 0 refers to 1 day; 1 refers to 7 days; 2 refers to 30 days; 3 refers to 60 days; 4 refers to 90 days; 5 refers to 182 days; and 6 refers to 365 days |
| Percentage of effective therapy days | 2 | A ratio of a number of days when the user uses the therapy device for no less than 4 hours to a total number of days of the iCode statistical period |
| Average daily use time | 2 | Average daily time for the user to use the device in the iCode data statistical period |
| P95 | 2 | Average P95 in the iCode data statistical period |
| AHI | 2 | Average AHI in the iCode data statistical period |
| Percentage of high air leak time (greater than 90 LPM) | 2 | Average percentage of daily air leak time in the iCode data statistical period |
| Best 30 | 2 | A given maximum number of days when the user uses the therapy device for no less than 4 hours in a continuous 30-day time window in the iCode data statistical period |
| Check code | 3 | Check code |

In an optional embodiment of the present application, the step of performing legitimacy verification on the therapy data may specifically include the following steps.

In step S31, the therapy data is parsed to acquire a plaintext string and an original check code in the therapy data.

In step S32, a verification check code is generated by a preset algorithm according to the plaintext string acquired through parsing and the device identification of the therapy device.

In step S33, if the original check code is consistent with the verification check code, the therapy data is determined to pass the legitimacy verification; otherwise, the therapy data is determined to fail to pass the legality verification.

In step 303, the therapy data is saved if the therapy data passes the legitimacy verification; and the therapy data is discarded if the therapy data fails to pass the legitimacy verification.

In step 304, the therapy data is sent.

In step 305, parameter update information corresponding to the therapy data is received, wherein the parameter update information carries a latest therapy parameter acquired by updating the therapy parameter according to the therapeutic effect data, and the device identification corresponding to the therapy device.

In the embodiment of the present application, the parameter update information may also be transmitted according to the customized iCode information coding format above, and after the smart terminal receives the parameter update information from the server or the second client side, legitimacy verification may be performed on the parameter update information according to the same verification method as the therapy data to ensure the security of data transmission.

In conclusion, according to the embodiment of the present application, after the first client side receives the therapy data, legality verification may further be performed on the therapy data, and subsequent operations are allowed when the therapy data passes the legality verification; otherwise, the therapy data is discarded, so as to improve the security of data transmission. In addition, because the embodiment of the application can check the therapy data transmitted between the therapy device and the first client side according to a customized data format and a conventional algorithm, contents of the transmitted data can also be prevented from malicious tampering.

Third Method Embodiment

Figure 4:
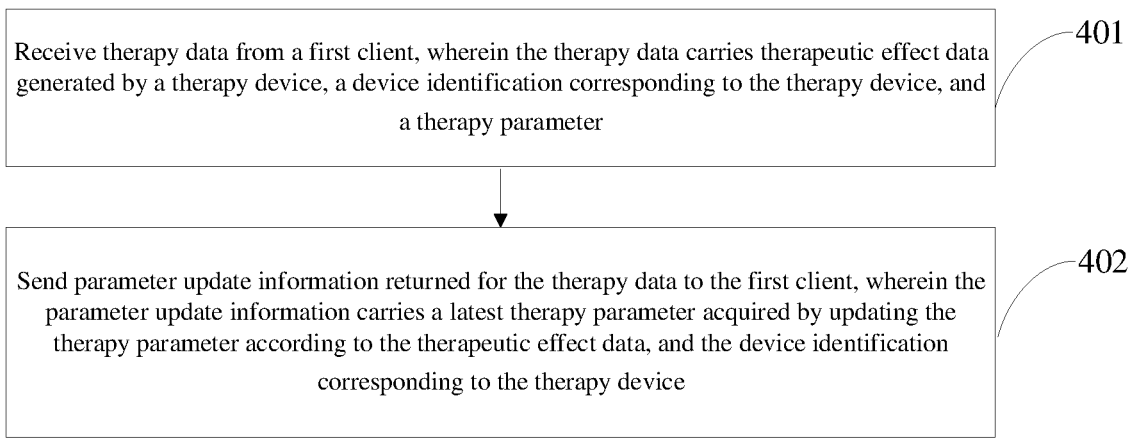
FIG. 4 is a flow chart of steps of an information processing method according to still another embodiment of the present application.

FIG. 4 illustrates a flow chart of steps of an information processing method according to still another embodiment of the present application. The method may be applied to a service, and may specifically include the following steps.

In step 401, therapy data from a first client side is received, wherein the therapy data carries therapeutic effect data generated by the therapy device, a device identification corresponding to the therapy device, and a therapy parameter.

In step 402, parameter update information returned for the therapy data is sent to the first client side, wherein the parameter update information carries a latest therapy parameter acquired by updating the therapy parameter according to the therapeutic effect data, and the device identification corresponding to the therapy device.

In specific application, a software service platform can be installed in the server, and the first client side may be butted with the software service platform to upload therapy data of a patient (including compliance data and therapeutic effect data) in real time. The software service platform can manage therapy data uploaded by the patient, and allows doctors or health care providers to log in the software service platform to access these therapy data. The doctors or health care providers determine whether to amend therapy schedule of the patient by analyzing the compliance data and therapeutic effect data in the therapy data. If the therapy schedule needs to be amended, then the updated therapy parameter is set on the software service platform, and the parameter update information is sent to the corresponding first client side through the software service platform.

In an optional embodiment of the present application, the therapy data may carry a patient identification corresponding to the first client side. The method may further include the following step.

The patient identification and therapy data corresponding to the patient identification are saved.

In order to enable the doctor to quickly view the required therapy data of the patient, in the embodiment of the present application, when a user uploads the therapy data to the server by using the first client side, the therapy data may carry the patient identification corresponding to the first client side. In this way, when the server receives the therapy data, a correspondence between the therapy data and the patient identification can be saved. The patient identification may specifically be unique identification information such as an account number and a name registered by the user. For example, if the patient identification is a patient account registered by the user, the patient account number and therapy data corresponding to the patient account number may be saved in the server.

In another optional embodiment of the present application, the method may further include the following steps.

In step 41, a therapy data acquisition request from a second client side is received, wherein the therapy data acquisition request carries a patient identification.

In step S42, therapy data corresponding to the patient identification is sent to the second client side, wherein the therapy data carries therapeutic effect data generated by a therapy device, a device identification corresponding to the therapy device, and a therapy parameter.

In the embodiment of the present application, the patient identification and the therapy data corresponding to the patient identification may be saved in the server. A doctor can send a therapy data acquisition request to the server through the second client side, the therapy data acquisition request carries the patient identification, so as to acquire the therapy data corresponding to the patient identification.

After the server receives the therapy data acquisition request from the second client side, the therapy data corresponding to the patient identification is acquired by searching, and the searched therapy data is returned to the second client side, so that the doctor can view the required therapy data in the second client side.

In specific application, in order to ensure the safety and confidentiality of the therapy data of the patient, a doctor whitelist may be pre-established in the server, and the doctor whitelist includes a doctor identification that is allowed to access the therapy data in the server. The therapy data acquisition request may also carry a doctor identification in addition to the patient identification, and the server queries the doctor whitelist. If the doctor identification is present in the doctor whitelist, then the therapy data corresponding to the patient identification is sent to the second client side; otherwise, a reject message may be sent to the second client side.

Further, it is also possible to set an authority to add patients to the doctor. For example, the doctor having authority can set a mapping relationship between the doctor identification and the patient identification in the server, for example, a doctor A corresponds to a patient A, a patient B and a patient C; only the doctor A is allowed to acquire therapy data of the patient A, the patient B, and the patient C, and the doctor A is not allowed to acquire therapy data of other patients.

In another optional embodiment of the present application, the method may further include the following steps.

An analysis result and parameter update information returned for the therapy data from the second client side are received, wherein the analysis result is acquired by analyzing the therapeutic effect data, and the parameter update information carries a latest therapy parameter acquired by updating the therapy parameter according to the analysis result, and the device identification corresponding to the therapy device.

In specific application, after the server sends the therapy data corresponding to the patient identification to the second client side, the analysis result and the parameter update information returned for the therapy data from the second client side may also be received. Specifically, the doctor can view the received therapy data via the second client side, acquire the analysis result by analyzing the therapy data, update the therapy parameter according to the analysis result, and then return the latest therapy parameter updated to the server via the second client side.

It should be noted that a process of analyzing the therapy data to acquire the analysis result may be automatically performed by the first client side, the server, or the second client side, or may be manually analyzed by a doctor, and a manner of acquiring the analysis result is not limited in the embodiment of the present application.

In conclusion, the embodiment of the present application receives the therapy data from the first client side via the server, wherein the therapy data carries the therapeutic effect data generated by the therapy device, the device identification corresponding to the therapy device and the therapy parameter; sends parameter update information returned for the therapy data to the first client side; and can automatically collect the therapy data without requiring the doctor or the service personnel to carry a dedicated device to the user for data collection, or requiring the user to carry the therapy device to a designated place for data collection. Therefore, the therapy data of the user can be collected in time and conveniently through the embodiment of the present application without increasing the hardware costs.

Second Application Example

Figure 5:
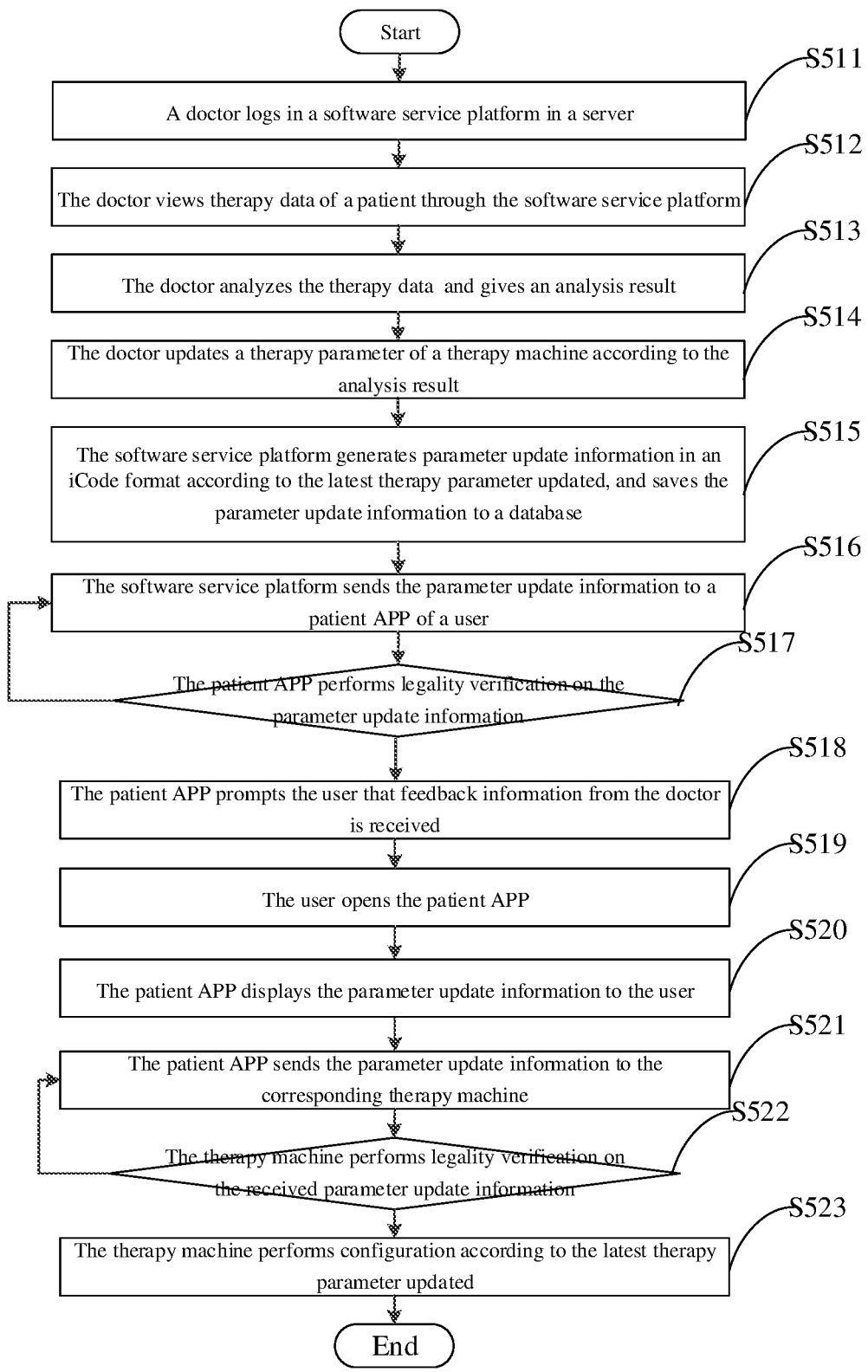
FIG. 5 is a schematic flow chart of transmitting parameter update information of a software service platform to a therapy machine according to the present application.

A process of transmitting the parameter update information of the server to the therapy machine through the first client side is described below with reference to a specific example. FIG. 5 illustrates a schematic flow chart of transmitting parameter update information of a software service platform to a therapy machine according to the present application, which may specifically include the following steps.

In step S511, a doctor logs in the software service platform in a server.

In step S512, the doctor views therapy data of a patient through the software service platform, including compliance data and therapeutic effect data.

In step S513, the doctor analyzes the compliance data and the therapeutic effect data of the patient, and gives an analysis result.

In step S514, the doctor updates a therapy parameter of the therapy machine according to the analysis result.

In step S515, the software service platform generates parameter update information in an iCode format according to the latest therapy parameter updated, and saves the parameter update information to a database.

In step S516, the software service platform sends the parameter update information to a patient APP of a user.

In step S517, the patient APP performs legality verification on the received parameter update information. If the parameter update information passes the legality verification, step S518 is performed; otherwise, step S516 is performed.

In step S518, the patient APP prompts the user to receive feedback information from the doctor, such as parameter update information.

In step S519, the user opens the patient APP.

In step S520, the patient APP displays the parameter update information to the user.

In step S521, the patient APP sends the parameter update information to the corresponding therapy machine.

In specific application, after receiving the parameter update information, the patient APP may prompt the user to open the therapy machine and establish a wireless connection with the patient APP. After the patient APP detects the connection with the therapy machine, the patient APP may send the parameter update information to the therapy machine.

In step S522, the therapy machine performs legality verification on the received parameter update information. If the parameter update information passes the legality verification, step S523 is performed; otherwise, step S521 is performed.

In step S523, the therapy machine is configured according to the latest therapy parameter updated.

Fourth Method Embodiment

Figure 6:
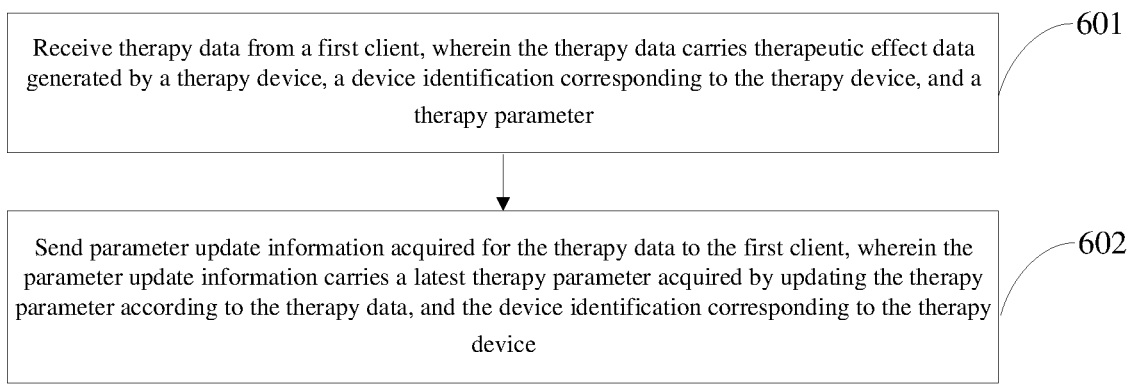
FIG. 6 is a flow chart of steps of an information processing method according to yet another embodiment of the present application.

FIG. 6 illustrates a flow chart of steps of an information processing method according to yet another embodiment of the present application. The method may be applied to a second client side, and may specifically include the following steps.

In step 601, therapy data from a first client side is received, wherein the therapy data carries therapeutic effect data generated by a therapy device, a device identification corresponding to the therapy device, and a therapy parameter.

In step 602, parameter update information acquired for the therapy data is sent to the first client side, wherein the parameter update information carries a latest therapy parameter acquired by updating the therapy parameter according to the therapy data, and the device identification corresponding to the therapy device.

In practical application, a traditional way for a doctor or a medical health care provider to view therapy data of a patient is to sit in front of a computer of a hospital and view the therapy data through a healthcare client side. However, in this case, it is necessary to keep in front of the client side, and it is necessary to equip each doctor with a computer, resulting in waste of human and material resources. Moreover, the doctor cannot view the therapy data of the patient anytime and anywhere, resulting in delays in patient therapy.

In order to solve the above problems, a doctor APP may further be installed in the second client side according to the embodiment of the present application, so as to acquire the therapy data of the patient through communications between the doctor APP and the software service platform or the first client side, and send the latest therapy parameter updated to the software service platform or the first client side via the doctor APP. In this way, the doctor can view the therapy data of the patient anytime and anywhere, and the time of the doctor can be saved, so that the doctor can give a therapy schedule to the patient according to the current therapy data of the patient in hospital, at home, and in a restroom, etc. Not only can manpower and material resources be saved, but also the therapy data of the patient can be viewed in time to treat the user in time. It can be understood that customized data format and verification method can be employed in the therapy data and the parameter update information transmitted between the doctor APP and the server or the second client side, so as to ensure the data integrity, validity, and security.

In an optional embodiment of the present application, the method may further include the following step.

A therapy data updating message from a server is received, wherein the therapy data updating message carries a patient identification.

In specific application, after the server receives the therapy data uploaded by a patient, a doctor corresponding to the patient uploading the therapy data can be found by a correspondence between the doctor identification and a patient identification, and then the therapy data updating message can be sent to the corresponding doctor to remind the doctor to view the latest therapy data uploaded by the patient in time.

In another embodiment of the present application, the method may further include the following step.

A latest therapy parameter is sent to the therapy device corresponding to the device identification, and the therapy device is set according to the latest therapy parameter.

According to the embodiment of the present application, the second client side can also directly transmit data with the therapy device through 3G, 4G, WiFi, or wired connection. The second client side can directly send the latest therapy parameter to the corresponding therapy device, automatically amend the original parameter in the therapy device, and set the therapy device according to the latest therapy parameter. The parameter can be amended without the first client side, or the manual amendment of the patient, which simplifies a parameter amendment process and a user operation process, and brings great convenience to the user.

In conclusion, the embodiment of the present application can receive the therapy data from the first client side via the second client side, wherein the therapy data carries the therapeutic effect data generated by the therapy device, the device identification corresponding to the therapy device and the therapy parameter; and send the parameter update information corresponding to the therapy data to the first client side. In this way, the doctor can view the therapy data of the patient anytime and anywhere, and the time of the doctor can be saved, so that the doctor can update the therapy parameter for the patient according to the current therapy data of the patient in hospital, at home, and in a restroom, etc. Not only can manpower and material resources be saved, but also the therapy data of the patient can be viewed in time to treat the user in time.

Third Application Example

Figure 7:
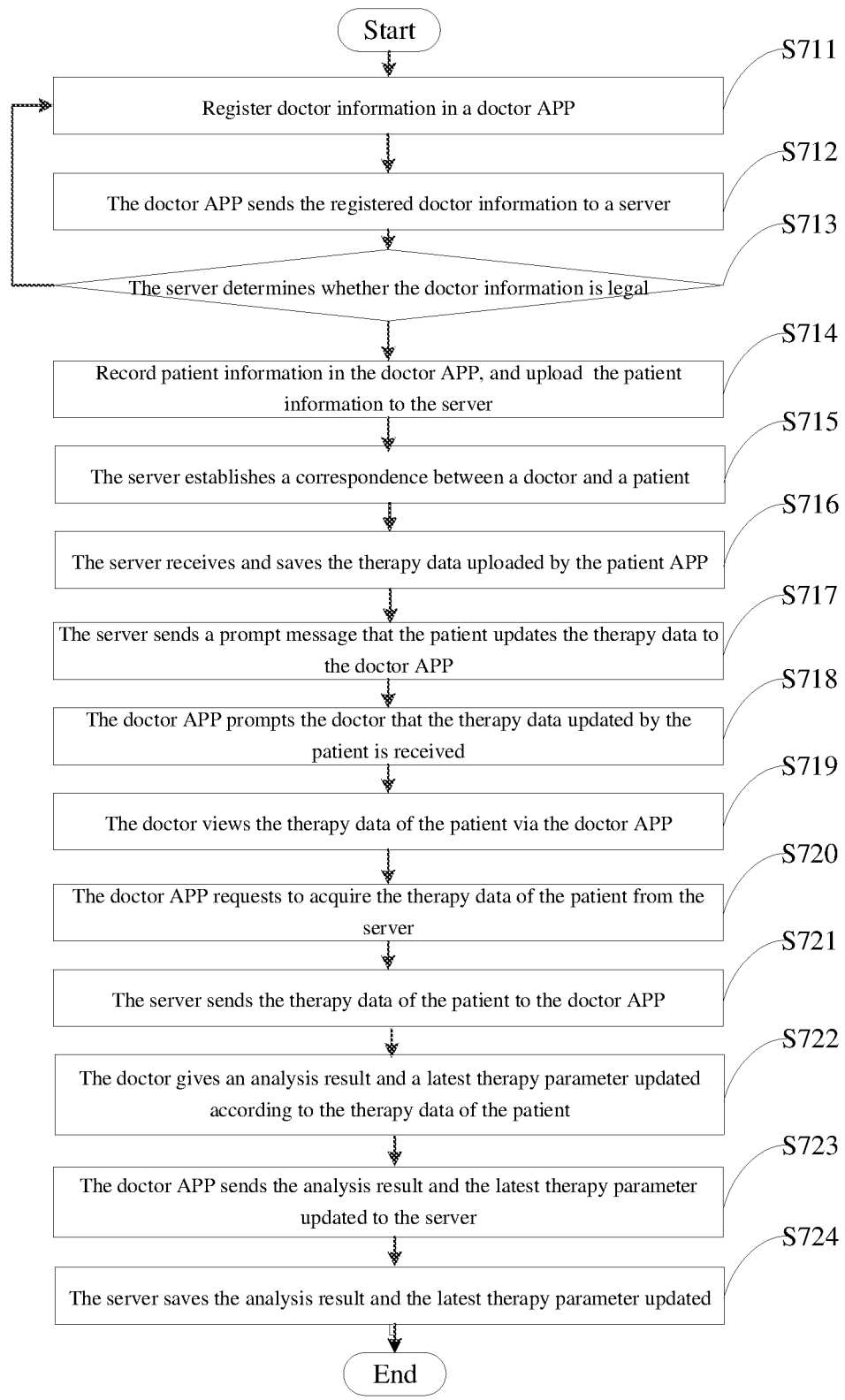
FIG. 7 is a schematic flow chart of a communication process between a doctor APP and a server according to the present application.

A communication process between the second client side and the server of the present application will be described below with reference to THE specific example. FIG. 7 illustrates a schematic flow chart of a communication process between a doctor APP and a server according to the present application, which may specifically include the following steps.

In step S711, doctor information is registered in the doctor APP, wherein the doctor information includes a doctor identification.

In step S712, the doctor APP sends the registered doctor information to the server.

In step S713, the server determines whether the doctor information is legal; if yes, step S714 is performed; otherwise, step S711 is performed.

In specific application, an authority of the doctor can be configured and managed. For example, a doctor whitelist can be set in the server in advance, and a doctor identification that is allowed to acquire the therapy data is stored in the whitelist. Similarly, an authority of the patient can be set, and can be added by the doctor, and only the patient added by the doctor has the authority to upload therapy data to the server.

In step S714, patient information is recorded in the doctor APP, and uploaded to the server.

Specifically, the registered doctor can log in the doctor APP and record the patient information under his/her name, for example, the patient identification can be added.

In step S715, the server establishes a correspondence between the doctor and the patient.

Specifically, a correspondence between the doctor identification and the patient identification can be established.

In step S716, the server receives and saves the therapy data uploaded by the patient APP.

Specifically, the therapy data may include a patient identification, as well as compliance data and therapeutic effect data of the patient. The server determines an authority corresponding to the patient identification. If the patient identification has the authority to upload the therapy data, the server receives and saves the therapy data uploaded by the patient; otherwise, the server returns a rejection message to the patient APP.

In step S717, the server sends a prompt message that the patient updates the therapy data to the doctor APP.

Specifically, the server finds a corresponding doctor identification according to the patient identification, and sends the prompt message that the therapy data is updated to the doctor APP corresponding to the doctor identification.

In step S718, the doctor APP prompts the doctor that the therapy data updated by the patient is received.

Specifically, if a patient uploads new therapy data, the doctor APP can issue a prompt so that the doctor can know the therapy condition of the patient in time.

In step S719, the doctor vies the therapy data of the patient via the doctor APP.

Specifically, one doctor may correspond to multiple patients, and the doctor may select a patient in a patient list and view therapy data of the patient.

In step S720, the doctor APP requests to acquire the therapy data of the patient from the server.

Specifically, the doctor APP sends a therapy data acquisition request to the server, wherein the request carries the patient identification of the patient selected by the doctor.

In step S721, the server sends the therapy data of the patient to the doctor APP.

The server acquires the therapy data of the patient according to the patient identification and sends the therapy data to the doctor APP.

In step S722, the doctor gives an analysis result and a latest therapy parameter updated according to the therapy data of the patient.

Specifically, the doctor can fill in evaluations of each index according to the therapy data, and generate a professional stage therapy report for the patient to view.

For example, the doctor analyzes the therapy data, for example: respiratory rate, ventilation, expiratory pressure, inspiratory pressure, respiratory events, and other data or corresponding waveforms; and amend the therapy parameters according to the analysis results of the therapy data, for example: adjusting one or more therapy parameters such as expiratory pressure, inspiratory pressure, and target tidal volume.

In step S723, the doctor APP sends the analysis result and the latest therapy parameter updated to the server.

In step S724, the server saves the analysis result and the latest therapy parameter updated.

The server can send the latest therapy parameter to the corresponding patient APP, and then send the latest therapy parameter to a ventilator through the patient APP, thereby amending parameters of the ventilator.

It should be noted that, for the sake of simple description, the method embodiments are all expressed as a series of action combinations, but those skilled in the art should understand that the embodiments of the present application are not limited by the described action sequences, because certain steps may be performed in other sequences or concurrently according to the embodiments of the present application. Secondly, those skilled in the art should also understand that the embodiments described in the specification are all preferred embodiments, and the actions involved are not necessarily required by the embodiments of the present application.

First Apparatus Embodiment

Figure 8:
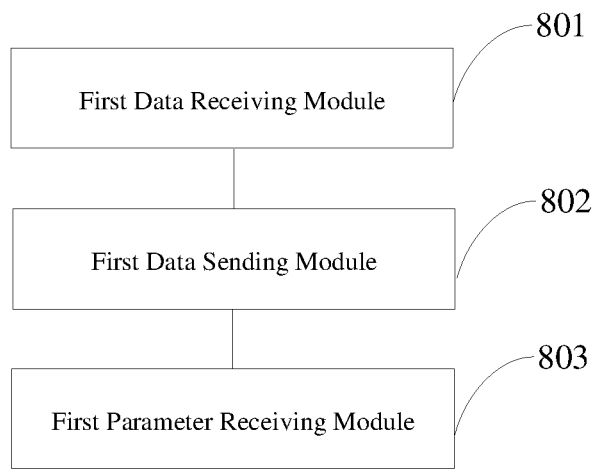
FIG. 8 is a structural block diagram of an information processing apparatus according to one embodiment of the present application.

FIG. 8 illustrates a structural block diagram of an information processing apparatus according to one embodiment of the present application, which is applied to a first client side. In the embodiment of the present application, the device may specifically include:

a first data receiving module 801 configured to receive therapy data from a therapy device, wherein the therapy data carries therapeutic effect data, a device identification corresponding to the therapy device, and a therapy parameter;

a first data sending module 802 configured to send the therapy data; and a first parameter receiving module 803 configured to receive parameter update information corresponding to the therapy data, wherein the parameter update information carries a latest therapy parameter acquired by updating the therapy parameter according to the therapeutic effect data, and the device identification corresponding to the therapy device.

In an optional embodiment of the present application, the apparatus may further include:

a verification module configured to, after receiving the therapy data from the therapy device, perform legitimacy verification on the therapy data; and a determining module configured to save the therapy data if the therapy data passes the legitimacy verification; and discard the therapy data if the therapy data fails to pass the legitimacy verification.

In another optional embodiment of the present application, the verification module may specifically include:

a data parsing submodule configured to parse the therapy data to acquire a plaintext string and an original check code in the therapy data;

a check code generating submodule configured to generate a verification check code by a preset algorithm according to the plaintext stringacquired through parsing and the device identification of the therapy device; and a verification submodule configured to, if the original check code is consistent with the verification check code, determine that the therapy data passes the legitimacy verification; otherwise, determine that the therapy data fails to pass the legality verification.

In another optional embodiment of the present application, the apparatus may further include:

an analysis module configured to analyze the therapy data to acquire an analysis result;

an analysis result sending module configured to send the analysis result, wherein the analysis result carries the device identification corresponding to the therapy device, and the therapy parameter; and a second parameter receiving module configured to receive the parameter update information corresponding to the analysis result, wherein the parameter update information carries a latest therapy parameter acquired by updating the therapy parameter according to the analysis result, and the device identification corresponding to the therapy device.

In yet another optional embodiment of the present application, the apparatus may further include:

a first parameter setting module configured to send the latest therapy parameter to the therapy device corresponding to the device identification, and set the therapy device according to the latest therapy parameter.

In yet another optional embodiment of the present application, the first data receiving module may specifically include:

a wireless receiving submodule configured to receive the therapy data from the therapy device via short-range wireless communication.

Second Apparatus Embodiment

Figure 9:
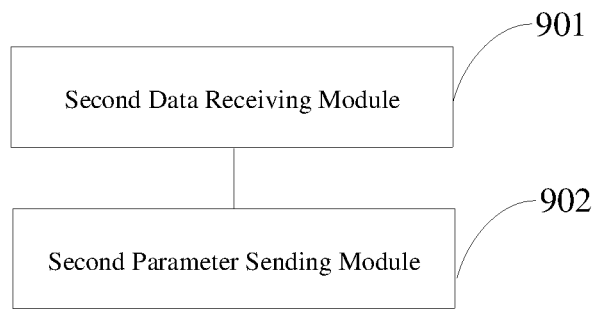
FIG. 9 is a structural block diagram of an information processing apparatus according to another embodiment of the present application.

FIG. 9 illustrates a structural block diagram of an information processing apparatus according to another embodiment of the present application, which is applied to a second client side. In the embodiment of the present application, the device may specifically include:

a second data receiving module 901 configured to receive therapy data from a first client side, wherein the therapy data carries therapeutic effect data generated by the therapy device, a device identification corresponding to the therapy device, and a therapy parameter; and a second parameter sending module 902 configured to send parameter update information acquired for the therapy data to the first client side, wherein the parameter update information carries a latest therapy parameter acquired by updating the therapy parameter according to the therapy data, and the device identification corresponding to the therapy device.

In an optional embodiment of the present application, the apparatus may further include:

a second parameter setting module configured to send the latest therapy parameter to the therapy device corresponding to the device identification, and set the therapy device according to the latest therapy parameter.

The various embodiments in the present specification are described in a progressive manner, and each embodiment focuses on differences from other embodiments, and the same similar parts between the various embodiments can be referred to each other.

With regard to the apparatus in the above embodiments, the specific manner in which the respective modules perform the operations has been described in detail in the embodiment relating to the method, and will not be explained in detail herein.

The device embodiments described above are merely illustrative, wherein the units described as separate components may or may not be physically separate, and the components displayed as units may or may not be physical units, i.e. may be located in a place, or it can be distributed to multiple network units. Some or all of the modules may be selected according to actual needs to achieve the objectives of the present application. Those of ordinary skill in the art can understand and implement without any creative effort.

Other embodiments of the present application will be readily apparent to those skilled in the art. The present application is intended to cover any variations, uses, or adaptations of the application, which are in accordance with the general principles of the application and include common general knowledge or common technical means in the art that are not disclosed in the disclosure. The specification and examples are to be regarded as illustrative only, the scope of the invention is defined by the claims.

It is to be understood that the invention is not limited to the details of the details and the scope of the application is limited only by the appended claims.

The above is only the preferred embodiment of the present application, and is not intended to limit the present application. Any modifications, equivalent substitutions, improvements, etc. made within the spirit and principles of the present application are included in the protection of the present application.

The above is a detailed description of an information processing method and apparatus provided by the present application. The principles and implementation manners of the present application are described in the specific examples. The description of the above embodiments is only used to help understand the present application. The method and its core concept may be understood by those skilled in the art, according to the idea of the present application, there will be changes in the specific implementation manner and the scope of application. In summary, the contents of this application is not explained as a limitation of the invention.

The invention claimed is:

1. An information processing method applied to a first client side, wherein the first client side is a smart terminal on a patient side, the information processing method comprising:
   receiving therapy data from a ventilation therapy device, wherein the therapy data carries therapeutic effect data, a device identification corresponding to the ventilation therapy device, and a therapy parameter;
   sending the therapy data;
   receiving parameter update information corresponding to the therapy data, wherein the parameter update information carries a latest therapy parameter acquired by updating the therapy parameter according to the therapeutic effect data, and the device identification corresponding to the ventilation therapy device;
   performing legitimacy verification on the therapy data after receiving the therapy data from the ventilation therapy device; and
   saving the therapy data if the therapy data passes the legitimacy verification and discarding the therapy data if the therapy data fails to pass the legitimacy verification,
   wherein the step of performing the legitimacy verification on the therapy data comprises:
   parsing the therapy data to acquire a plaintext string and an original check code in the therapy data;
   generating a verification check code by a preset algorithm according to the plaintext string acquired through parsing and the device identification of the ventilation therapy device; and
   determining that the therapy data passes the legitimacy verification if the original check code is consistent with the verification check code and determining that the therapy data fails to pass the legality verification if the original check code is not consistent with the verification check code.

2. The method according to claim 1, further comprising:
   analyzing the therapy data to acquire an analysis result;
   sending the analysis result, wherein the analysis result carries the device identification corresponding to the ventilation therapy device, and the therapy parameter; and
   receiving the parameter update information corresponding to the analysis result, wherein the parameter update information carries a latest therapy parameter acquired by updating the therapy parameter according to the analysis result, and the device identification corresponding to the ventilation therapy device.

3. The method according to claim 1, further comprising:
   sending the latest therapy parameter to the ventilation therapy device corresponding to the device identification and setting the ventilation therapy device according to the latest therapy parameter.

4. The method according to claim 1, wherein the step of receiving therapy data from a ventilation therapy device comprises:
   receiving the therapy data from the ventilation therapy device via short-range wireless communication.

5. An information processing method applied to a second client side, wherein the second client side comprises a smart terminal on a doctor side, the information processing method comprising:
   receiving therapy data from a first client side, wherein the first client side is a smart terminal on a patient side, and the therapy data carries therapeutic effect data generated by a ventilation therapy device, a device identification corresponding to the ventilation therapy device, and a therapy parameter; and
   sending parameter update information acquired for the therapy data to the first client side, wherein the parameter update information carries a latest therapy parameter acquired by updating the therapy parameter according to the therapy data, and the device identification corresponding to the ventilation therapy device,
   wherein after the first client side receives the therapy data from the therapy device, the first client side performs legitimacy verification on the therapy data, saves the therapy data if the therapy data passes the legitimacy verification and discards the therapy data if the therapy data fails to pass the legitimacy verification,
   wherein the step of performing the legitimacy verification on the therapy data by the first client side comprises:
   parsing the therapy data by the first client side to acquire a plaintext string and an original check code in the therapy data;
   generating a verification check code by the first client side by a preset algorithm according to the plaintext string acquired through parsing and the device identification of the ventilation therapy device; and
   determining that the therapy data passes the legitimacy verification by the first client side if the original check code is consistent with the verification check code, and determining that the therapy data fails to pass the legality verification by the first client side if the original check code is not consistent with the verification check code.

6. The method according to claim 5, further comprising:
   sending the latest therapy parameter to the ventilation therapy device corresponding to the device identification and setting the ventilation therapy device according to the latest therapy parameter.

7. A first client side device for information processing, wherein the first client side device is a smart terminal on a patient side device, the first client side device comprising:
   a memory having instructions stored thereon;
   a processor configured to execute the instructions to perform operations, comprising:
   receiving therapy data from a ventilation therapy device, wherein the therapy data carries therapeutic effect data, a device identification corresponding to the ventilation therapy device, and a therapy parameter;
   sending the therapy data;

receiving parameter update information corresponding to the therapy data, wherein the parameter update information carries a latest therapy parameter acquired by updating the therapy parameter according to the therapeutic effect data, and the device identification corresponding to the ventilation therapy device;

after receiving the therapy data from the ventilation therapy device, performing legitimacy verification on the therapy data; and saving the therapy data if the therapy data passes the legitimacy verification and discarding the therapy data if the therapy data fails to pass the legitimacy verification, wherein the performance of the legitimacy verification on the therapy data comprises:

parsing the therapy data to acquire a plaintext string and an original check code in the therapy data;

generating a verification check code by a preset algorithm according to the plaintext string acquired through parsing and the device identification of the ventilation therapy device; and determining that the therapy data passes the legitimacy verification if the original check code is consistent with the verification check code, and determining that the therapy data fails to pass the legality verification if the original check code is not consistent with the verification check code.

8. The first client side device according to claim 7, the operations further comprising:

analyzing the therapy data to acquire an analysis result;

sending the analysis result, wherein the analysis result carries the device identification corresponding to the ventilation therapy device, and the therapy parameter; and receiving the parameter update information corresponding to the analysis result, wherein the parameter update information carries a latest therapy parameter acquired by updating the therapy parameter according to the analysis result, and the device identification corresponding to the ventilation therapy device.

9. The first client side device according to claim 7, the operations further comprising:

sending the latest therapy parameter to the ventilation therapy device corresponding to the device identification and setting the ventilation therapy device according to the latest therapy parameter.

10. The first client side device according to claim 7, wherein the operation of receiving therapy data from a ventilation therapy device comprises:

receiving the therapy data from the ventilation therapy device via short-range wireless communication.

* * * * *